United States Patent [19]

Maimon

[11] Patent Number: 5,011,779
[45] Date of Patent: Apr. 30, 1991

[54] APPARATUS FOR RAPID DEPOSITION OF TEST SAMPLES ON AN ABSORBENT SUPPORT

[75] Inventor: Jonathan Maimon, Rego Park, N.Y.

[73] Assignee: Long Island Jewish Medical Center, New Hyde Park, N.Y.

[21] Appl. No.: 418,784

[22] Filed: Oct. 2, 1989

Related U.S. Application Data

[63] Continuation of Ser. No. 146,570, Jan. 21, 1988, abandoned.

[51] Int. Cl.$^5$ ............................................. C12M 1/32
[52] U.S. Cl. ............................... 435/293; 436/809; 436/530; 422/101; 422/104; 435/301
[58] Field of Search ............... 422/109, 101, 104; 435/40, 293, 301; 436/180, 530, 807, 809

[56] References Cited

U.S. PATENT DOCUMENTS

| | | | |
|---|---|---|---|
| 3,667,917 | 6/1972 | Brandt | 436/162 |
| 3,843,053 | 10/1974 | Thoden | 436/162 |
| 4,161,508 | 7/1979 | Janchen | 436/162 |
| 4,264,560 | 4/1981 | Natelson | 422/66 |
| 4,341,498 | 7/1982 | Ellis | 413/3 |
| 4,554,839 | 11/1985 | Hewett et al. | 422/100 |
| 4,557,903 | 12/1985 | McCormick | 422/101 |
| 4,713,165 | 12/1987 | Conover et al. | 204/411 |

FOREIGN PATENT DOCUMENTS

| | | | |
|---|---|---|---|
| 185330A | 12/1984 | European Pat. Off. | 422/100 |
| 3226112 | 10/1983 | Fed. Rep. of Germany | 436/162 |

OTHER PUBLICATIONS

Schleicher et al., *Minifold* Bulletin No. 358 3/583, 1981.

*Primary Examiner*—David L. Lacey
*Assistant Examiner*—Lyle Alfandary-Alexander
*Attorney, Agent, or Firm*—Kenyon & Kenyon

[57] ABSTRACT

The disclosure is directed to a method and apparatus for depositing a plurality of discrete liquid assay test samples onto an absorbent assay support. Pursuant to the invention, a guide and positioning device is provided to receive and position a device for dispensing a plurality of discrete test samples such that the dispensing device is operable to dispense the plurality of test samples in accordance with a predetermined pattern. A planar absorbent assay support device is positioned at a position which is vertically spaced and aligned below the guide and positioning device to receive the discrete test samples dispensed by the dispensing device. In this manner, a plurality of discrete test sample spots may be rapidly absorbed onto the absorbent assay support device in accordance with the predetermined pattern for efficient, simultaneous processing in a chosen immunoassay system.

4 Claims, 4 Drawing Sheets

APPARATUS FOR RAPID DEPOSITION OF TEST SAMPLES ON AN ABSORBENT SUPPORT

This is a continuation of co-pending application Ser. No. 146,570, filed on Jan. 21, 1988, now abandoned.

BACKGROUND OF THE INVENTION

The invention is directed to a method and apparatus, which may be in kit form, for accurate and rapid mass processing of large numbers of test samples absorbed onto an absorbent support, such as a nitrocellulose paper support, or other suitable support. The apparatus of the invention is particularly well suited for rapid assaying of large numbers of experimental cell cultures grown in standard tissue culture plates having 96 individual culture wells arranged in 8 rows of 12 wells each.

Sensitive assay systems for screening cell culture test samples for the presence of a specific product are known which entail adsorption of a small quantity of a culture medium onto nitrocellulose paper, or other suitable adsorbent support means, and assay of the absorbed material in situ. Immunoassay methods known in the art for assay of material absorbed on, e.g., nitrocellulose supports, include radioimmunoassay (RIA) and enzyme-linked-immunosorbent assay (ELISA). Still other known assays which are performed on test samples absorbed on a paper support include the use of labeled RNA and DNA probes to assay culture samples absorbed on nitrocellulose for the presence of a complimentary segment of DNA.

When a test sample is to be assayed for the presence of a specific antibody, an immunoassay is performed whereby a radio-labelled antigen or an antigen linked with an enzyme is contacted with the test sample which is absorbed onto the support. Binding of the antigen to the absorbed test sample indicates the presence of the desired antibody product. Binding of the antigen can be conveniently determined in situ by a visible color reaction (ELISA) or by counting the radioactivity (RIA) that is bound to the test sample absorbed on the nitrocellulose, depending upon the type of immunoassay system used. Although these assay systems are reliable and easily performed, they are labor-intensive, and become quite burdensome and expensive when mass screening of many test culture samples is involved.

In current hybridoma methodology, a mouse myeloma cell is fused with a spleen cell of a mouse immunized with a specific antigen in order to obtain an individual cell line that is producing a myeloma antibody to that antigen in tissue culture. One must fuse a large number ($10^7$–$10^8$) of myeloma cells with an equally large population of spleen cells, thus producing heterogeneous antibodies. Of those cells which fuse into immortal hybrid cells ("hybridomas"), only a small fraction produce an antibody to the desired antigen. It is therefore necessary to isolate from the heterogeneous population of experimental hybridomas, the one hybridoma cell which produces a monoclonal antibody to the specific antigen.

In order to isolate the one specific hybridoma cell from the heterogeneous experimental population, the experimental cell culture is distributed among a plurality of wells in tissue culture plates. Typically, these plates have 96 wells per plate. The cells are incubated and divide in their individual wells, and a sample is taken from the culture medium in each well and then assayed for the presence of the specific desired antibody. If a sample from a well tests positive for the specific antibody, the cells are taken up and the population divided by redistribution into other plates of, e.g., 96 wells. The cells are incubated in these wells and the assay is repeated again for the detection of samples in wells containing cells producing the desired antibody. In this manner, antibody-positive wells are repeatedly identified and subcloned, until all the cells in a given well are derived from a single cell, i.e., the cell culture is monoclonal.

This repetitive subcloning and assaying of antibody producing wells to obtain a pure monoclonal hybridoma is tedious and, as heretofore practiced, is highly labor-intensive. A small quantity of test culture sample must be taken from each well and absorbed onto an adsorbent assay support such as nitrocellulose paper, and each absorbed test sample spot must then be assayed by an RIA or ELISA procedure.

In an ELISA system, a small sample is withdrawn from each cell culture well and absorbed onto nitrocellulose paper. This first application provides any antibodies that are being produced in the culture medium. Next, a blocking solution of BSA, gelatin or other solution is applied to block nonspecific protein binding by the paper. To do this, the entire sheet of nitrocellulose paper is submerged in the blocking solution. The third step is the application of the specific antigen to the nitrocellulose paper having the cell culture sample absorbed thereon. The antigen is usually conjugated to an enzyme which can be assayed by a color reaction. If there is an antibody present in the cell culture absorbed onto the nitrocellulose paper, the antibody binds the antigen and thereby also the conjugated enzyme. The fourth step is the application of the substrate for the conjugated enzyme. As a final result of the reaction of the enzyme and its substrate, a measurable color develops on the nitrocellulose paper where the test sample was absorbed. A color reaction is visible on the nitrocellulose paper when the specific antibody to the antigen conjugated to the enzyme is present in the absorbed cell culture test sample. The intensity of the color is proportional to the amount of specific antibody in the cell culture.

To perform an RIA procedure, a sample is withdrawn from a test culture well and absorbed onto nitrocellulose paper, to immobilize any antibodies which might be present. The nitrocellulose paper with absorbed sample is then submerged in a blocking solution. A radio-labelled antigen is then applied to the nitrocellulose paper containing the absorbed test culture sample. The radio-labelled antigen is bound to the test sample only if the specific antibody to the antigen is present in the test sample. Radioactivity bound to the nitrocellulose paper through the test sample is counted in a gamma or liquid scintillation counter.

SUMMARY OF THE INVENTION

It is an object of the present invention to provide an apparatus and a method for rapid mass processing of large numbers of assay test samples absorbed onto an adsorbent assay support means, such as a nitrocellulose paper support.

The apparatus and method of the invention are particularly suited for rapid screening of experimental cell cultures, such as hybridomas or transformed cells, in which, in the absence of the invention, hundreds or thousands of individual samples of culture wells in tissue culture plates must be tediously screened for those few cells producing a desired bioproduct, as discussed above. However, the invention may also be utilized to perform any assay of a test sample on an adsorbent support, such as nitrocellulose paper, as e.g., isotopic assays, and nonisotopic assays including competitive or non-competitive enzyme-linked immunoabsorbent assays, fluorescent immunoassays, chemiluminescent assays, bioluminescent assays, and the like.

In accordance with the invention, a guide apparatus is provided for simultaneously positioning and applying a number of discrete liquid assay test samples in a predetermined pattern (e.g., the pattern of cell culture wells in a standard cell culture plate) on an adsorbent assay support. Generally, the invention comprises a guide and positioning means to simultaneously receive and position a means for dispensing a plurality of discrete test samples (e.g., a twelve tip multichannel pipette) in said predetermined pattern; and means to receive, support and position a planar adsorbent assay support means (e.g., a sheet of nitrocellulose paper) at a position which is vertically spaced and aligned below the guide and positioning means. In this manner, a plurality of discrete test samples may be simultaneously deposited on the planar absorbent assay support means to provide a plurality of discrete test sample spots absorbed on the assay support in accordance with the predetermined pattern.

In one advantageous embodiment of the invention, the nitrocellulose paper or other assay support means has dimensions which match the dimensions of a standard (commercially available) tissue culture plate having 96 wells arranged in 8 rows of 12 wells each. The paper is marked in a manner to indicate the orientation of the paper to correctly correspond to the 96 well cell culture plate. In accordance with this embodiment of the invention, the predetermined pattern of the guide and positioning means includes 96 dispensing means positions arranged in 8 rows of 12 positions, corresponding to the row configuration of the tissue culture plate. The liquid dispensing means is preferably a 12-tip multi-channel pipette whose tips fit the dimensions of the 12 wells in a single row of the cell culture plate as well as the 12 guide positions of each row of the guide and positioning means. Accordingly, the 12-tip multi-channel pipette is used to readily, simultaneously transfer discrete test samples, one from each of the wells of the cell culture plate, to corresponding positions on the guide and positioning means for deposition of discrete test samples onto the absorbent support positioned below the guide and positioning means. The apparatus of the invention therefore provides an assay support template, such as a nitrocellulose assay template, with discrete test sample spots positioned to correspond to the positions of the 96 wells in a cell culture plate.

Many such nitrocellulose assay templates may be rapidly prepared, one for each 96-well-cell-culture plate. The nitrocellulose assay template with discrete absorbed culture samples is removed from the guide and positioning means and immersed into a bath container for simultaneous processing with other templates according to the immunoassay system chosen. The bath container may accomodate, for example, as many as ten nitrocellulose templates in a removable template organizer and may be processed through a sequence of bath containers to perform a desired assay. Thus, up to 960 assays of cell culture test samples may be readily processed simultaneously in one unit. After completion of the assay baths, each of the nitrocellulose templates may be rapidly scanned for any color reaction if an ELISA system was used.

In accordance with another feature of the invention, a multiple punch device is provided for simultaneously detaching and separating the plurality of discrete test samples absorbed on the adsorbent assay support template in said predetermined pattern and delivering the detached test samples to individual receiver means arranged in accordance with the predetermined pattern. Thus, if the assay employed involves the binding of a radio-label to the absorbed test spots, the nitrocellulose assay template is placed in the multiple punch device for detaching and separating the plurality of test sample spots. The multiple punch device punches out all the test spots at a single press and blows all the cut discs into the individual receiver means arranged in the predetermined pattern and suitable for use in a radiolabel counter.

DETAILED DESCRIPTION

Figure 1:
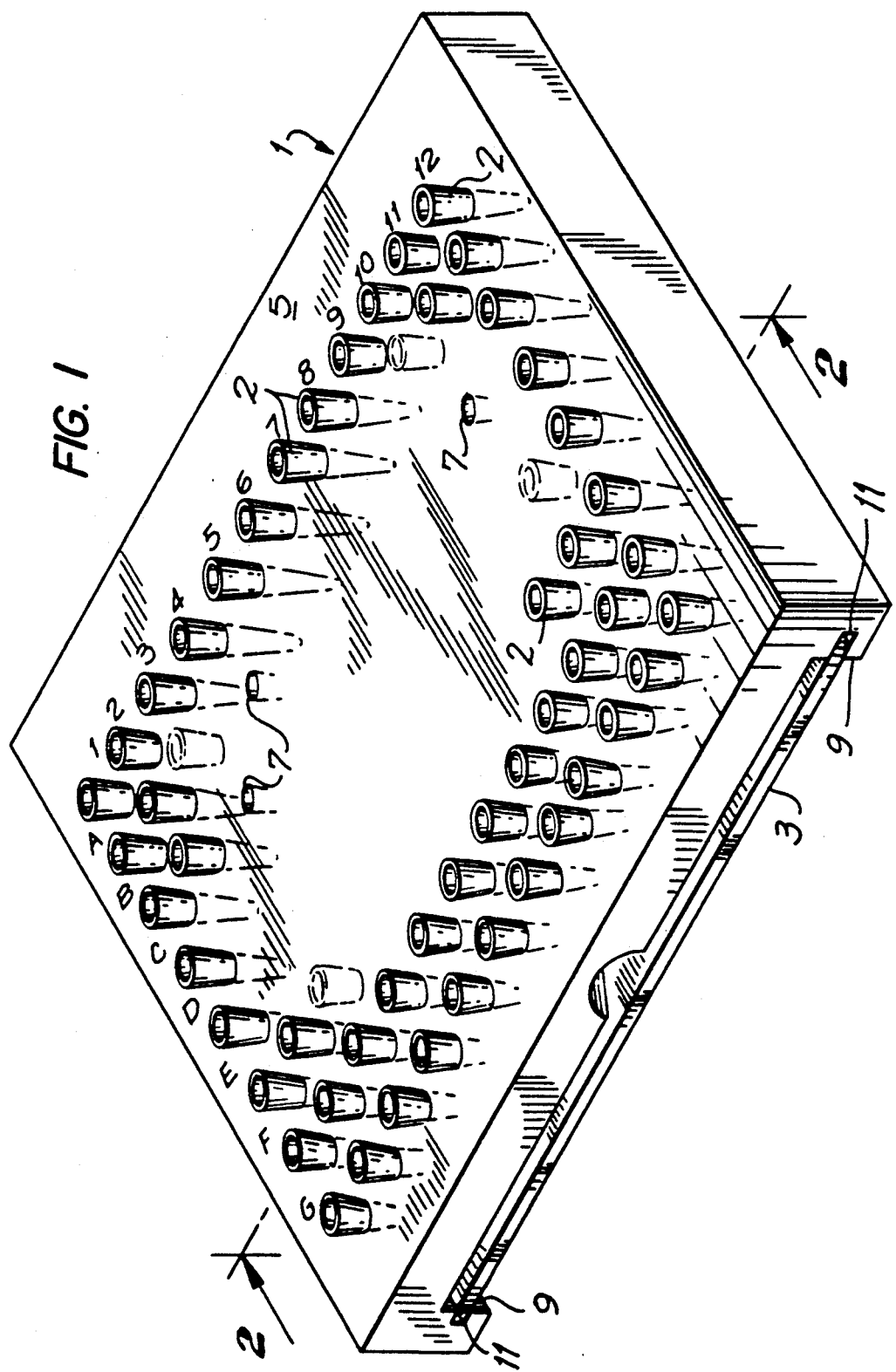
FIG. 1 is a perspective view of a preferred embodiment of a guide and positioning means according to the invention for applying and positioning a plurality of liquid test samples on an absorbent assay support means.
Figure 2:
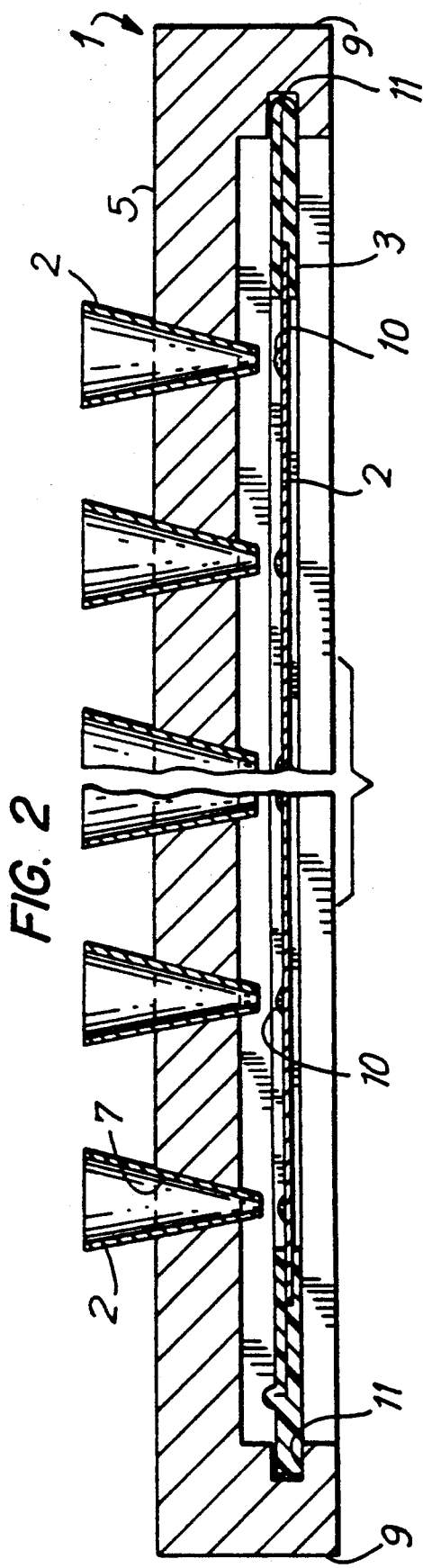
FIG. 2 is a side cross-sectional view taken generally along line 2—2 of FIG. 1.

Referring now to the drawings and initially to FIG. 1, there is illustrated an apparatus for simultaneously applying and positioning a plurality of liquid assay test samples in a predetermined pattern on an absorbent support. The apparatus comprises a guide and positioning means 1 to simultaneously receive and position a plurality of liquid dispensing elements 2, and a cooperating planar absorbent assay support frame 3 to receive and position a planar absorbent assay support 4, such as a sheet of nitrocellulose paper (see FIGS. 2 & 3), within the guide and positioning means 1.

As shown in FIG. 1, the guide and positioning means 1 comprises a planar top member 5 having a plurality of bore-type passages 7 formed there through. Each of the passages 7 communicates between the upper and lower surfaces of the top member 5 and is desirably shaped to receive outlet means of the liquid dispensing elements 2, such as, e.g., pipettes. It is preferred that the bore-type passages 7 are generally conical in shape, with the base of the cone being located in the upper surface of the planar member 5. More particularly, it is preferred that the bore-type passages 7 be so dimensioned that the tips of standard pipettes, preferably used as the dispensing elements 2 to transfer assay samples, will protrude through and project beyond the bottom surface of the top planar member 5.

In accordance with the invention, the bore-type passages 7 are arranged in the top member 5 in a predetermined pattern, preferably in a rectangular pattern of rows and columns. Since the apparatus of the invention is intended to be used in conjunction with conventional cell culture plates, which have 96 sample wells arranged in 8 rows having 12 wells in each row, the passages 7 are preferably arranged in 8 rows (A-H), each having 12 of the passages 7 (1-12) spaced relative to one another to correspond to the sample wells in the conventional culture plate.

A pair of vertical legs 9 are provided to support the planar top member 5 above a surface. As shown in FIG. 1, the vertical legs 9 comprise two elongated vertical legs 9 extending the full length of the planar member 5. It should be understood, however, that other suitable support means can be used.

A pair of grooves 11, or any other equivalent support arrangement, are formed, one in each of the vertical legs 9, to support the absorbent support frame 3 at a predetermined, vertically spaced distance below the bottom of the planar number 5. More particularly, it is desired that the absorbent support frame 3 be supported below the protruding tips of the dispensing elements 2 at a distance such that, when test samples are applied to the planar absorbent assay support 4, separate discrete "spots" f samples 10 are formed on the absorbent support 4. When the bore-type passages 7 are in a pattern corresponding to the conventional 96-well culture plate, and when the volume of each sample applied to the absorbent support is 5 microliter, it has been found that the distance between the tips of the dispensing elements 2 located in the bores 7 and the upper surface of the absorbent assay support 4 is preferably 2 mm.

Figure 3:
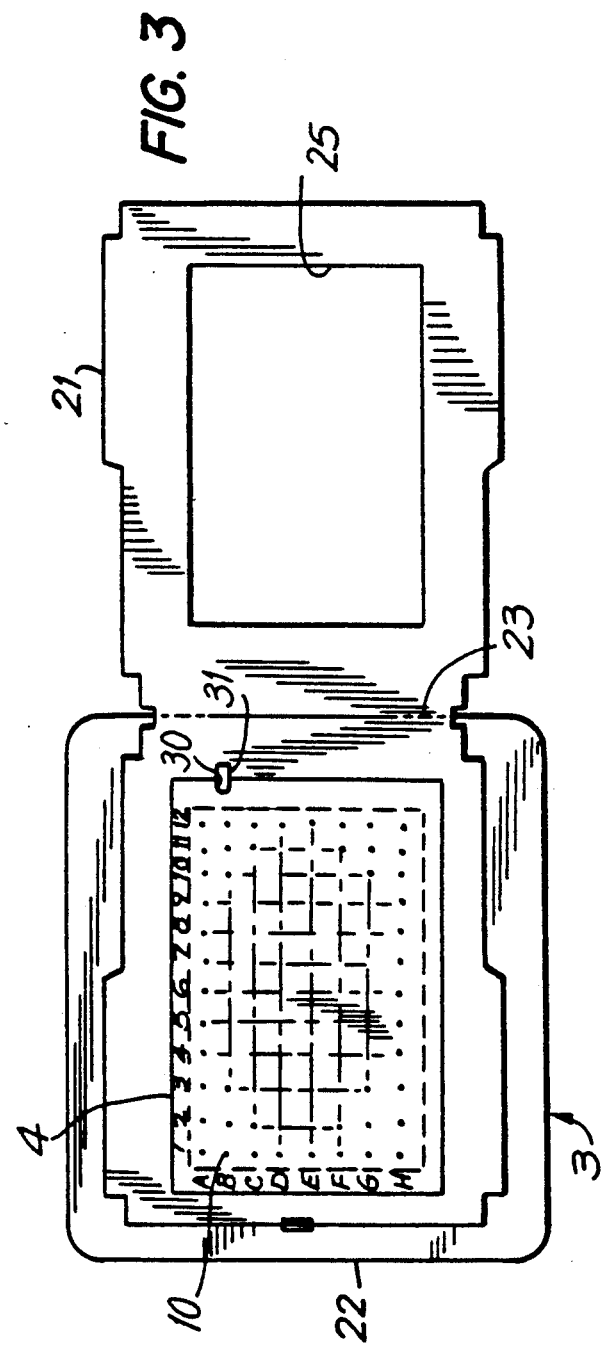
FIG. 3 is a plan view of a preferred embodiment of a slide-like frame means according to the invention to hold the absorbent support means.

Pursuant to the invention, the absorbent support frame 3 is used to maintain the planar absorbent assay support 4 in a proper alignment relative to the pattern of the bore-type passages 7 when the frame 3 is supported by the grooves 11. Referring now to FIG. 3, the absorbent support frame 3 comprises a slide-like frame having upper and lower cooperating frame members 21 and 22, respectively, designed to clasp and hold an absorbent assay support 4, such as a sheet of nitrocellulose paper, between them. As shown in FIG. 3, the frame members 21 and 22 are desirably hinged by a hinge connection 23 at one end so that they may be opened to insert the absorbent assay support 4 into the frame member 22 whereupon the frame member 21 is rotated about the hinge connection 23 to close the slide-like frame 3 and thereby clamp the absorbent assay support 4 between them.

The frame member 22 is dimensioned such that, when the absorbent assay support 4 is held in the frame 3, an opening 25 in the frame member 21 provides an exposed surface area of the assay support 4 which is greater than the area under the preselected pattern of bore-type passages 7 in the planar member 5, and sufficiently wide such that discrete the sample "spots" 10 of desired dimensions may be formed. When the bore-type passages 7 are in the configuration of the conventional 96-well culture plate, the exposed area of the nitrocellulose assay support 4 is preferably at least 125 mm by 80 mm. As discussed above, the absorbent assay support 4 may include a notch 30 for matching to a corresponding element 31 on the frame member 22 to insure that the nitrocellulose paper is properly oriented when the frame 3 is inserted into the grooves 11.

The invention is preferably designed to allow 5 microliter of each of the 96 test samples to be dispensed and simply adsorbed onto the nitrocellulose paper below, and thereby create 96 one cm diameter neighboring rings or sample spots 10 that do not overlap, and which are arranged in a pattern on the assay support 4 corresponding to the pattern of the wells in the cell culture plate from which the samples were derived. The absorbed discrete samples 10 therefor provide a nitrocellulose template.

Figures 4, 5:
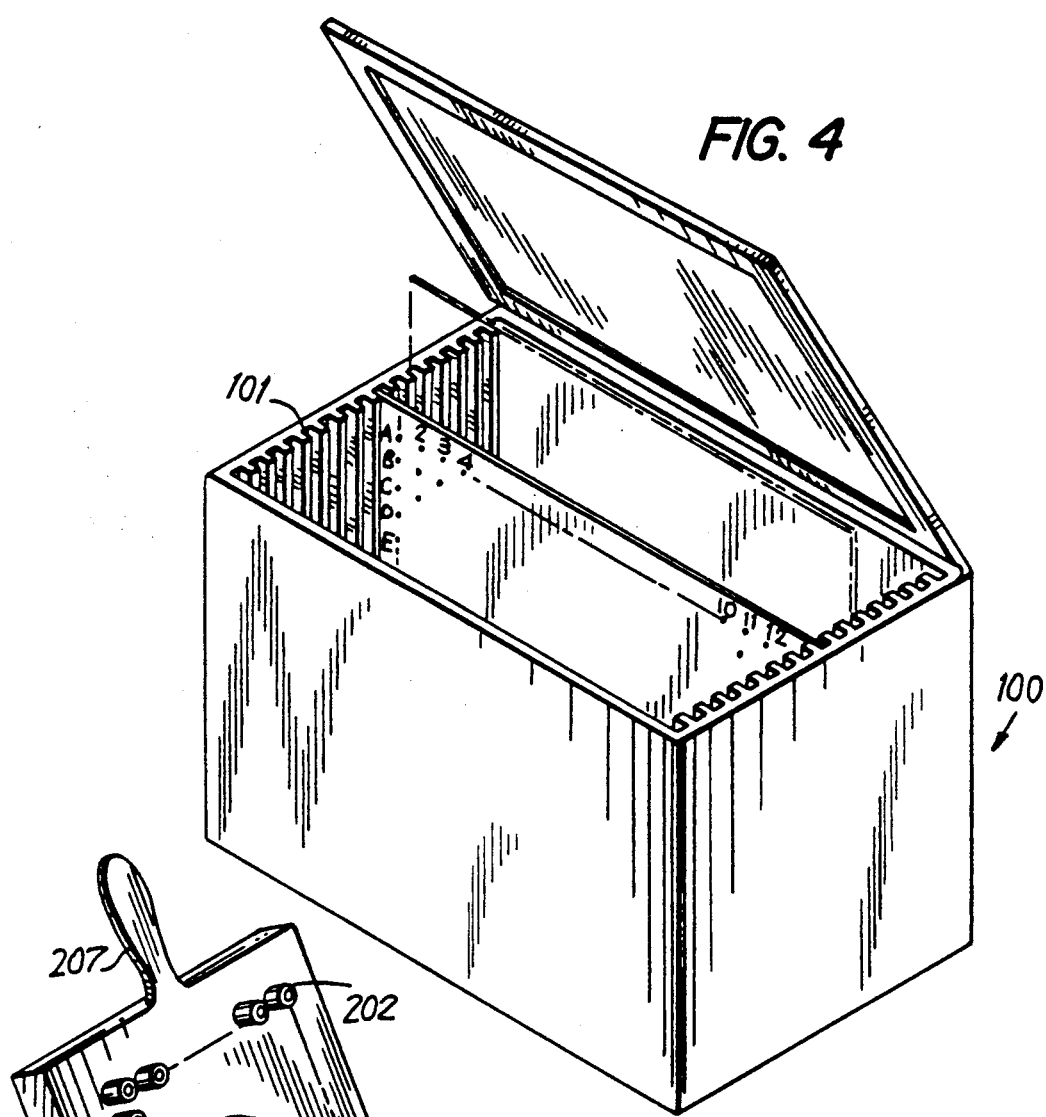
FIG. 4 is a perspective view of a template holder to accomodate a plurality of absorbent assay support means for simultaneous processing according to the invention.
FIG. 5 is a perspective view of a punch apparatus for detaching and separating a plurality of test sample spots absorbed on an absorbent assay support means.
Figure 6:
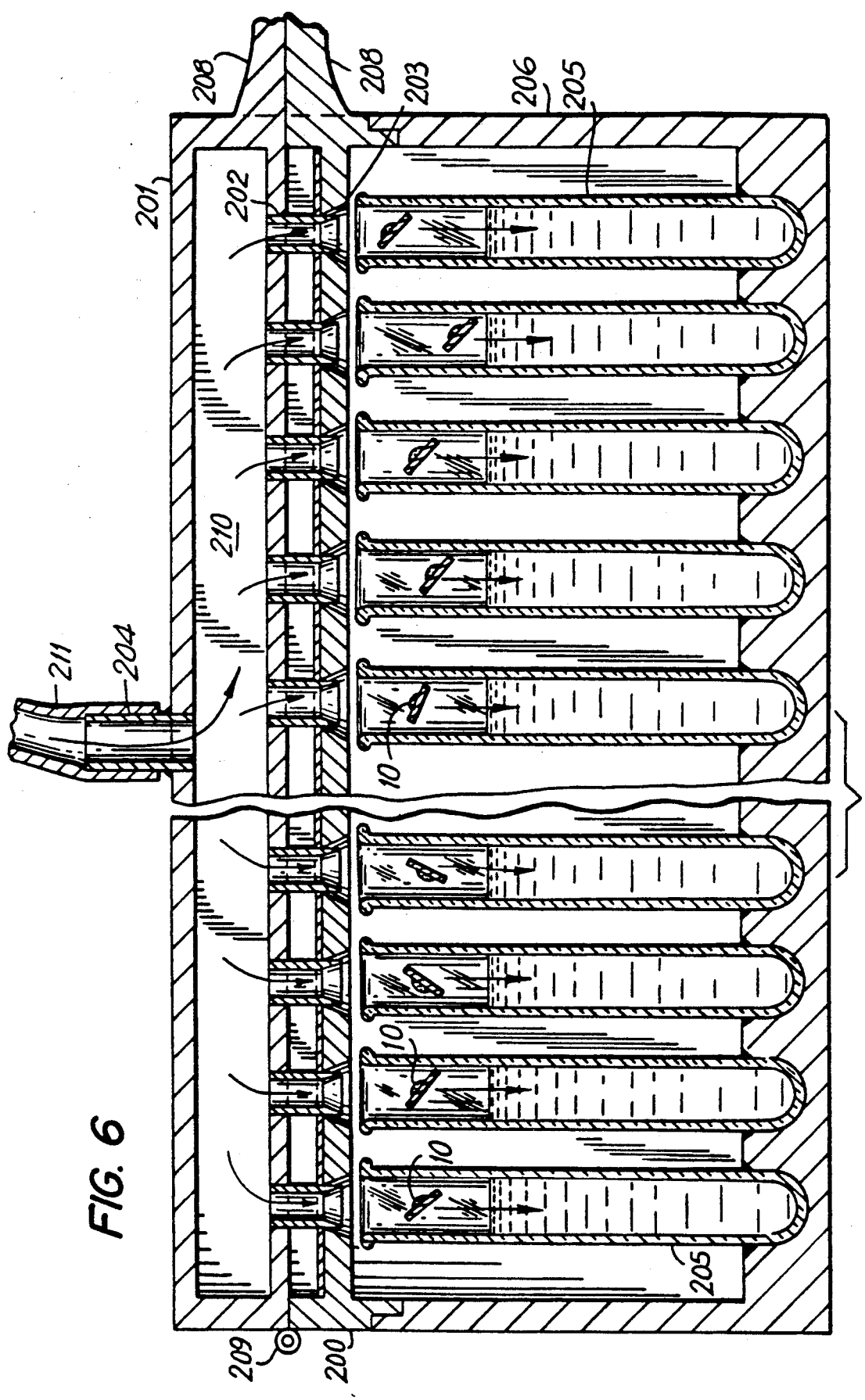
FIG. 6 is a side cross-sectional view taken generally along line 6—6 of FIG. 5.

Referring now to FIG. 4, a template holder 100, which may be reusable or disposable, is constructed to hold several, e.g. ten, nitrocellulose assay supports 4 after deposition of the test samples 10. The assay supports 4 are inserted into guide slots 101 such that the inserted supports 4 can be simultaneously submerged into a bath or baths for RIA or ELISA processing, as will be described below.

A multiple punch device is provided and illustrated in FIG. 5. The multiple punch device is used in an RIA assay and comprises a base 200 in which a sheet of nitrocellulose paper 4 with the absorbed discrete test samples 10 can be placed. A member 201 is provided with individual means 202 for punching out 96 paper discs, each of which is arranged to circumscribe one of the absorbed test sample spots 10. The member 201 is connected by a hinge 209 to the base 200. Corresponding openings 203 are formed in the base 200 such that the spots punched out by the individual means 202 when the member 201 is rotated about the hinge 209 in a punching operation may be removed from the punch device. An air blow nozzle 204 is mounted at the top of the hinged member 201 to blow air from an air tube 211 through the cutting means 202 via a manifold 210 and thereby fascilitate passage of the 96 punched discs having the test samples 10 thereon through the openings 203 and into 96 tubes 205 arranged in a rack 206 positioned below the base 200. The tubes 205 are arranged in the rack 206 and marked to correspond to the 96 wells in the original cell culture plates and also sequentially left to right. The tubes can go directly into a gamma counter or placed in larger tubes to accommodate the specification of the gamma counter. A pair of handles 207, 208 are provided to facilitate the punching operation.

An RIA procedure using the apparatus of the present invention is performed as follows:

(1) The nitrocellulose assay support 4 is placed in the slide-like frame 3, in the correct orientation, as described above.

(2) The frame 3 containing the nitrocellulose assay support 4 is inserted into the grooves 11 of the vertical legs 9 for holding and positioning the frame 3 vertically below the top planar member 5.

(3) Test samples of each culture media are pipetted, preferably with a 12-tip multichannel pipette, from each row of twelve wells in a culture plate. The 12 tips 2 of the multichannel pipette are positioned by the conical bore-type passages 7 in the planar member 5 and the test samples in the tips 2 are simultaneously ejected to dispense the discrete test samples of the 12 tips for each row to the vertically aligned absorbent assay support 4 positioned below the planar member 5. This is continued until 96 positions on the nitrocellulose absorbent support 4 have a discrete test sample deposited thereon in accordance with the pattern of the passages 7. (At the beginning of the screening of the cell cultures, one may have to repeat this application from the same culture wells to the same spots to assure sufficient amount of antibodies or other desired biochemical on every spot.) If desired, the use of a hot air dryer (do not exceed 56°

C.) speeds up the drying of absorbents and minimizes the ring on the nitrocellulose template paper.

(4) The completed nitrocellulose support 4 with the associate frame 3 is removed from the guide and positioning means 1 and placed vertically in the template holder 100.

(5) When all the slots 101 in the template holder 100 are filled, it is placed in a bath container containing a blocking solution and incubated overnight or shorter over a rotary shaker.

(6) The template holder 100 is then removed from the bath container containing the blocking solution and dipped into another bath container containing a buffer for a short rinse.

(7) The entire holder 100 is then dipped into another bath container containing $^{125}$I antigen (or other isotope) in a 20 mM P-N buffer containing albumin, 1% fish skin gelatin or other blocking solution. The concentration and the specific activity of the radio-labelled antigen needed to provide a sufficient number of counts per minute at each test spot in which an antibody is present is determined empirically. This is then shaken at room temperature overnight or shorter (determined empirically).

(8) The template holder 100 is thereafter placed in another bath container containing 20 mM phosphate buffer PH 7.5 containing 0.5% NP 40 to remove all nonspecifically bound radio-labelled antigen.

(9) The template holder 100 is removed from the bath container of step 8 and placed in an oven or air dryer at 37° C. to dry the nitrocellulose paper (10 to 15 minutes).

(10) Each sheet of nitrocellulose paper is placed in the base of a multiple punch device 200. The loaded punch is placed on a test tube rack 206 with 96 pre-marked tubes 205 mounted therein, and the top punch means 201 is pressed closed to cut out the 96 discs. An air tubing 211 (lab source) is connected to the nozzle 204 in the top of the punch to blow the 96 paper discs through the openings 203 and into the 96 tubes 205.

(11) The premarked tubes 205 are placed into larger tubes to fit into an automatic gamma counter. Each tube is counted for 30 seconds to 1 minute, depending on the level of radioactivity in each tube. (If another isotope is to be used, count with a liquid sintilation counter, depending on the type and energy spectrum of the emitted radiation.)

(12) The discs having high counts per minute (above background and blank paper) are identified and correlated with the correct well in the culture plate.

If an ELISA system employing a visible color reaction is to be used for the assay, there is no need to cut the 96 test spots out of the nitrocellulose paper with the punch. Test samples containing the desired antibody are identified by visual inspection of the whole nitrocellulose paper for the development of spots of positive color reaction at the discrete test sample spots deposited on the nitrocellulose paper pursuant to the method of the invention. The locations of the positive test sample spots are correlated to the correct well in the culture plate using the grid on the frame 3.

In a preferred embodiment of the invention, there is provided a removable plastic liner for the bore-type passages 7. The liner may comprise a disposable plastic liner formed to include conical wells to fit the bore-type passages 7 so as to preserve the sterility of the dispensing elements 2 for reuse or to avoid contamination of the planar member 5 and the passages 7 from radioactive or contagious material.

A flat horizontal adjustable heater to fit underneath the pipette guide may be used to quickly dry the culture samples absorbed to nitrocellulose paper, in order to allow multiple applications (on same spots) of cell culture media. Multiple applications are useful at the beginning of the cell culture screening procedure when the desired biochemical, e.g., antibody, concentration is very low, as described above. By the time the last row of culture samples is applied to the nitrocellulose paper, culture samples can be reapplied to the first row.

What is claimed is:

1. A non-vacuum apparatus for mass processing of test samples comprising a guide and positioning means having a top and side surfaces wherein one of the sides has a horizontal groove constructed so as to slidably receive an absorbent material support frame and in the top there are a plurality of openings disposed in a rectangular pattern; an absorbent material support frame slidably mounted in said groove below said openings for movement into and out of said means, said frame having a pair of rectangular frame members hingedly connected together in overlying relationship with at least an upper frame member having an aperture therein; and a planar absorbent array support removably mounted in said frame between said frame members and below said openings for receiving liquid test samples therefrom under gravity within said aperture of said upper frame member.

2. An apparatus as set forth in claim 1 wherein each of said frame members has an aperture to permit exposure of said array support to said dispensing elements.

3. An apparatus as set forth in claim 1 wherein each of said openings is of conical shape.

4. An apparatus as set forth in claim 1 wherein said array support has a notch on one side and wherein a lower one of said frame member has an element thereon for positioning in said notch to orient said array support in said frame.

* * * * *